United States Patent [19]

Matsumoto et al.

[11] Patent Number: 4,675,071
[45] Date of Patent: Jun. 23, 1987

[54] METHOD OF PREPARING THIN CRYSTAL OR FILM

[75] Inventors: Mutsuo Matsumoto, Nara; Kuniaki Nagayama, Tokyo, both of Japan

[73] Assignee: JEOL Ltd., Tokyo, Japan

[21] Appl. No.: 780,420

[22] Filed: Sep. 26, 1985

[30] Foreign Application Priority Data

Sep. 29, 1984 [JP] Japan .................. 59-205132

[51] Int. Cl.⁴ ............................ C30B 7/00
[52] U.S. Cl. ........................... 156/621; 65/99.2; 65/99.3; 204/180.1; 204/182.2; 156/607; 156/DIG. 82; 156/DIG. 88; 156/DIG. 89
[58] Field of Search ........... 156/DIG. 82, DIG. 89, 156/DIG. 88, 621, 607; 65/99.2, 99.3; 204/180.1, 180.2

[56] References Cited

U.S. PATENT DOCUMENTS

| | | | |
|---|---|---|---|
| 3,721,543 | 3/1973 | Classen et al. | 65/99.2 |
| 4,012,216 | 3/1977 | Marchand | 65/99.3 |
| 4,148,622 | 4/1979 | Heitzer et al. | 65/99.3 |
| 4,174,207 | 11/1979 | Gagne | 65/99.3 |
| 4,547,259 | 10/1985 | Santini | 156/607 |

OTHER PUBLICATIONS

"A New Technique for Investigating Lipid Protein Films" by Peter Fromherz, *Biochim. Biophys. Acta*, 225 (1971), 382-387.

McGraw-Hill Encyclopedia of Science and Technology, vol. 8, p. 289, col. 2, lines 18-20, McGraw-Hill Book Company, New York, 1971.

*Primary Examiner*—John Doll
*Assistant Examiner*—Lori S. Freeman
*Attorney, Agent, or Firm*—Webb, Burden, Robinson & Webb

[57] ABSTRACT

A stratum of mercury is formed in an atmosphere, for example, helium gas. A liquid material is dropped to the surface of the mercury stratum. Since the surface tension of the mercury is larger than that of the liquid material, the liquid material rapidly spreads over the surface of the mercury stratum. As a result, a film is formed or a crystal grows on the surface of the mercury stratum. A DC voltage is applied between the liquid material and the mercury stratum. The resultant capillary electrical phenomenon momentarily spreads the liquid material over the surface of the mercury stratum. Thus, a good film is formed or a good crystal grows.

8 Claims, 1 Drawing Figure

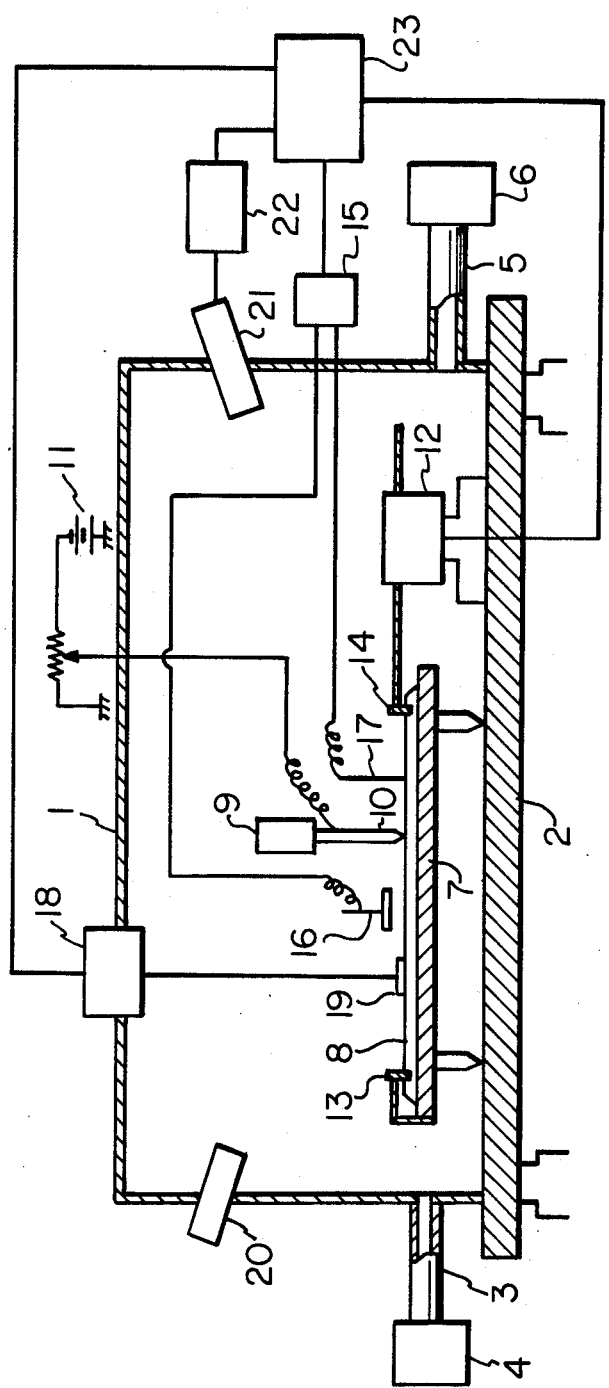

METHOD OF PREPARING THIN CRYSTAL OR FILM

FIELD OF THE INVENTION

The present invention relates to a method of preparing a thin crystal or film by forming a film of a liquid material or orientating its molecules in a two-dimensional manner.

BACKGROUND OF THE INVENTION

The Langmuir-Blodgett technique of the like is a well-known method of preparing a crystal or film as in "A new technique for investigating lipid protein films" by Peter Fromherz (*Biochim. Biophys. Acta* 225 (1971) 382–387. This technique was originally developed to prepare a two-dimensional film or crystal from a surfactant that is insoluble in water. In recent years, as an extended application of this technique a method of preparing crystals or films from molecules of materials other than surfactants has been proposed. According to this proposed method, a surfactant is spread over the surface of water in which such molecules are dissolved that will form a crystal or film. The dissolved molecules are attracted to the surfactant, and finally they orientate themselves together with the surfactant at the surface of water to form a two-dimensional crystal or film.

The crystal or film prepared by the aforementioned method contains the surfactant, as well as the desired molecules. Therefore, it is impossible to prepare a pure crystal or film by the method. Further, molecules capable of forming crystals or the like are restricted to those molecules attracting surfactants and so it is not possible to form crystals or the like from molecules not attracting surfactants. In addition, molecules that can act on surfactants are limited to those molecules which exist only near the surface of water and limited in amount, although the desired molecules are previously dissolved in water. Most of the molecules remain dissolved in water, making the efficiency of utilization of the molecules very low.

SUMMARY OF THE INVENTION

It is the main object of the present invention to provide a method of preparing a pure crystal or film from a liquid material.

It is another object of the invention to provide a method of preparing a crystal or film from a liquid material with a high efficiency of utilization.

It is a further object of the invention to provide a method of preparing a film from an organic solvent, a material dissolved in a solvent, an oily material, or any other liquid material.

In one aspect of the invention, a stratum of mercury is formed within an envelope that is placed in a certain atmosphere. A liquid material is caused to drop to the surface of the mercury film so that the liquid material spreads over the surface to prepare a thin crystal or film.

In a second aspect of the invention, a stratum of mercury is formed within an envelope that is placed in a certain atmosphere, a liquid material is dropped to the surface of the mercury film, and a voltage is applied between the liquid material and the mercury film so that the liquid material spreads over the surface of the mercury film to prepare a thin crystal or film.

In one feature of the invention, a stratum of mercury is formed within an envelope that is placed in an atmosphere of, for example, water vapor or helium gas, and a liquid material is dropped to the surface of the mercury film. Since the surface tension of the mercury is larger than that of the liquid material, the liquid material is rapidly spread over the surface of the mercury film. As a result, a film is formed or a crystal grows on the surface of the mercury film. A DC voltage is applied between the liquid material and the mercury film. The resultant capillary electrical phenomenon momentarily spreads the liquid material over the surface of the mercury film, producing an excellent film or crystal.

Other objects and features of the invention will appear in the course of the description thereof that follows.

BRIEF DESCRIPTION OF THE DRAWINGS

The single FIGURE shows an instrument for carrying out the method according to the invention.

PREFERRED EMBODIMENTS OF THE INVENTION

An example of instruments for carrying out the method of the invention is shown in the drawing. The instrument has an envelope 1 mounted on a vibration-proof base 2. The inside of the envelope 1 is evacuated by an appropriate vacuum pump 4 via an exhaust pipe 3. Helium gas is supplied into the envelope 1 from a helium gas source 6 through a communication pipe 5. A vessel 7 in which a thin film or crystal is formed is mounted on the bottom of the envelope 1. A stratum (layer, film or plate) of mercury 8 is formed on the top surface of the vessel 7. The surface of this mercury stratum 8 is made substantially planar by the action of gravity. A liquid material supplier 9 is disposed above the mercury stratum 8 and has a conductive nozzle 10 at its front end. A liquid material is dropped from the nozzle 10 to the mercury stratum 8. An appropriate voltage is applied to the nozzle 10 from a power supply 11. The film formed on the surface of the mercury stratum is compressed by a mechanical drive 12, which moves a moveable plate 14 on the surface of the mercury stratum relative to a stationary partition plate 13 to compress the film overlying the mercury stratum. A surface potential-measuring device 15 brings a probe 16 in the form of a plate and a stylus-like probe 17 close to the surface of the film formed on the mercury stratum 8 to measure the electric potential on the surface. An electronic balance 18 has a flat plate 19 that comes into contact with the surface of the film on the mercury stratum. The balance 18 acts to measure the surface tension on the formed, upper film. A laser 20 is mounted to the envelope 1 and emits a laser beam toward the surface of the film on the mercury stratum 8. The beam is reflected at the front and rear surfaces of the upper film, leading to interference of the laser waves. The interfering waves are then detected by a detector 21. The resultant signal is supplied to an arithmethic circuit 22 to determine the thickness of the film. The output signal from the arithmetic circuit 22 that varies depending on the thickness of the film, the signal from the balance 18 that varies depending on the surface tension of the film, and the signal from the measuring device 15 that varies depending on the potential on the film are all furnished to a control means 23 as consisting of a computer. The control means 23 controls tha compressor 12 according to its input signals which indicate the conditions of the film.

In the structure constructed as described above, the inside of the envelope 1 is evacuated by the vacuum pump 4 so that the inside is completely freed from contaminants. Then, helium gas is supplied into the envelope 1 from the helium gas source 6, and mercury is put on the vessel 7 within the envelope 1. Under the atmosphere of helium gas, a water solution of molecules for forming a crystal is dropped to the surface of the mercury stratum 8 from the liquid material supplier 9 via the nozzle 10. Because the surface tension of mercury is larger than that of water solution, the solution is rapidly spread over the surface of the mercury stratum, thus forming a quite thin film or crystal. At this time, the nozzle 10 is brought close to the surface of the mercury stratum 8 so that the water drop at the front end of the nozzle 10 comes into contact with the surface of the mercury stratum. In this state, a DC voltage of about a few voltages is applied between the nozzle and the mercury film 8 from the power supply 11. The resultant capillary electrical phenomenon reduces the surface tension to such an extent that it can be almost neglected. Since the mercury film and the water solution are rendered different widely in surface tension, the water solution is momentarily spread over the surface of the mercury stratum. Consequently, a quite uniform film or crystal is formed.

The water solution spreads over the surface of the mercury stratum 8 as described above. The conditions of the thin film formed on the mercury stratum 8 are measured by the electronic balance 18, the arithmetic circuit 22, and the surface potential-measuring device 15. The output signals from these components are fed to the control means 23, which controls the mechanical drive 12 according to its input signals. When it is found that the two-dimensional density or thickness of the film does not reach a prescribed value, the mechanical drive 12 moves the movable plate 14 toward the stationary partition plate 13 to increase the molecular density or thickness. The film or crystal formed in this way can be used in various applications. As an example, a portion of the formed film is transferred onto a mesh as a specimen for an electron microscope. Also, the film can be applied to a semiconductor or the like by immersing it in the mercury on which the film is formed.

While a preferred embodiment of the invention has been described using specific terms, such description is for illustrative purposes only, and it is to be understood that changes and variations may be made without departing from the spirit and scope of the invention. For example, in the above example water solution is dropped to the mercury stratum. Organic solvents, substances dissolved in organic solvents, oily matters, and other liquid matters may be used to form films, instead of the water solution. Also, in the above example the inside of the envelope is permeated with helium gas. Obviously, a film may be formed under the atmosphere of other gas, such as nitrogen, argon, oxygen, water vapor, or vaporized organic substance. Especially, control over the water vapor pressure is important to the formation of a film having a good crystallinity. As a modified example, a material may be dissolved in a volatile organic solvent to form a film, and then the solvent may be drived off by vaporization. During this process, control over the vapor pressure of the organic solvent inside the envelope is effective in forming a desired film.

As described thus far in detail, according to the invention, a liquid material is dropped to mercury having a large surface tension to prepare a film or crystal. Accordingly, it is possible to directly prepare a pure crystal or film that is more inactive at the interface with water than that formed using a surface active agent by the prior art method. Further, it is not necessary to dissolve the liquid material in water, but rather the liquid material is used as it is. Therefore, the efficiency of utilization of the liquid material is quite high. Furthermore, a crystal containing water may be formed. Additionally, since the liquid material is momentarily spread over the mercury film by the capillary electrical phenomenon, a good film or crystal can be formed.

We claim:

1. A method of preparing a thin crystal or film from a liquid material having a surface tension less than that of mercury, comprising the steps of:

forming a stratum of mercury within an envelope that is placed in an atmosphere comprising helium gas, argon gas, nitrogen gas, oxygen gas, water vapor or vaporized organic substance;

dropping a material selected from the group consisting of a water solution, an organic solvent, an oily material or a material dissolved in a solvent, said material being in liquid form and further having a surface tension less than that of mercury, to the surface of the mercury stratum so that said material spreads over the surface of the mercury stratum; and preparing a thin crystal or film of said material.

2. A method of preparing a thin crystal or film from a liquid material having a surface tension less than that of mercury, comprising the steps of:

forming a stratum of mercury within an envelope that is placed in an atmosphere comprising helium gas, argon gas, nitrogen gas, oxygen gas water vapor or vaporized organic substance;

dropping a material, selected from the group consisting of a water solution, an organic solvent, an oily material or a material dissolved in a solvent, said matrial being in liquid form and further having a surface tension less than that of mercury, to the surface of the mercury stratum; and applying a voltage between said material and the mercury stratum to spread said material over the surface of the mercury stratum; and preparing a thin crystal or film of said liquid material.

3. A method of preparing a thin crystal or film as defined in claim 1 or claim 2, wherein said atmosphere is formed by helium gas.

4. A method of preparing a thin crystal or film as defined in claim 1 or claim 2, wherein said atmosphere is formed by nitrogen gas.

5. A method of preparing a thin crystal or film as defined in claim 1 or claim 2, wherein said atmosphere is formed by vapor of an organic substance.

6. A method of preparing a thin crystal or film as defined in claim 1 or claim 2, wherein said atmosphere is formed by water vapor.

7. A method of preparing a thin crystal or film as defined in claim 1 or claim 2, wherein said material is dissolved in water.

8. A method of preparing a thin crystal or film as defined in claim 1 or claim 2, wherein said material is dissolved in an organic solvent.

* * * * *